United States Patent [19]

Schmitt et al.

[11] Patent Number: 5,009,231
[45] Date of Patent: Apr. 23, 1991

[54] MICROPROCESSOR CONTROLLED APPARATUS FOR THE NONINVASIVE DETERMINATION OF PERIPHERAL OUTFLOW AND FLOW DISTURBANCES

[75] Inventors: Hans J. Schmitt; Vladimir Blazek, both of Aachen, Fed. Rep. of Germany

[73] Assignee: Fa. Nattermann Arzneimittel GmbH, Cologne, Fed. Rep. of Germany

[21] Appl. No.: 26,607

[22] Filed: Mar. 17, 1987

[30] Foreign Application Priority Data

Mar. 18, 1986 [DE] Fed. Rep. of Germany ....... 3609075

[51] Int. Cl.$^5$ ................................................ A61B 5/00
[52] U.S. Cl. ................................ 128/633; 250/252.1; 356/39
[58] Field of Search ........ 128/633, 672, 634, 664–667; 250/252.1 A, 252.1 R; 356/39

[56] References Cited

U.S. PATENT DOCUMENTS

| 4,109,643 | 8/1978 | Bond et al. | 128/666 |
| 4,653,498 | 3/1987 | New, Jr. et al. | 128/633 |

Primary Examiner—William E. Wayner
Attorney, Agent, or Firm—Cushman, Darby & Cushman

[57] ABSTRACT

A measuring apparatus for the noninvasive determination of peripheral outflow and flow disturbances in the extremities of human beings includes at least one light transmitter for directing light onto the skin of a human subject and at least one light receiver for receiving reflected light as well as an evaluation and read-out circuit to ascertain the temporal course of blood outflow or inflow in the veins by measuring the changes in the reflected light. The evaluation and read-out circuit calibrates itself prior to measuring by raising the current flowing through the light transmitter or transmitters until the signal-to-noise ratio of the receiver has attained a specific value.

12 Claims, 5 Drawing Sheets

MICROPROCESSOR CONTROLLED APPARATUS FOR THE NONINVASIVE DETERMINATION OF PERIPHERAL OUTFLOW AND FLOW DISTURBANCES

CROSS-REFERENCE TO RELATED APPLICATIONS

The subject matter of the present application is related to that disclosed in applicant's commonly owned U.S. patent application Ser. No. 07/026,606, filed Mar. 17, 1987, now U.S. Pat. No. 4,836,212 and entitled "An Apparatus For the Noninvasive Determination And Acoustical Representation of the Dynamic Behavior of Peripheral Venous Hemodynamic," the disclosure of which is incorporated herein by reference.

BACKGROUND OF THE INVENTION

The present invention relates to a measuring apparatus for the noninvasive determination of peripheral outflow and flow disturbances in the extremities of human beings.

Measuring devices of this sort are disclosed in, by way of illustration, German Patent No. 31 00 610.8 or German Patent No. 33 18 746.0. In the measuring device disclosed in DE-PS 31 00 610.8, the temporal course of the reflected or dispersed back part of the radiation is evaluated in an analog manner and recorded by means of a recording device. In the measuring device disclosed in DE-PS 33 18 746.0, the analog signal is translated or converted into a digital signal by means of a transmission-reception data connection point circuit and transferred to a calculator device. The calculator device calculates the physical rating parameters for the analog light reflection curves. This measuring device is thus particularly suitable for conducting and evaluating a test series.

Both prior art measuring devices share the drawback that they cannot easily be constructed as hand-held, portable apparatuses: neither the recording device employed as disclosed in DE-PS 31 00 610.8 nor the common microcomputer with floppy disc drives, etc. disclosed in DE-PS 33 18 746.0 can be miniaturized to the extent that they can readily be built into a portable apparatus. Moreover, the power consumption of the prior art measuring devices is too high for portable apparatuses.

It is especially disadvantageous with regard to the prior art measuring devices that the operating staff determines the commencement and the termination of each measurement, thereby making subjective measurement errors possible.

SUMMARY OF THE INVENTION

In view of the above, it is an object of the present invention, among others, to provide a measuring apparatus for the noninvasive determination of peripheral outflow and flow disturbances in the extremities of human beings, permitting the design and construction of a compact, energy-saving apparatus, and, in addition, an apparatus having "measuring and evaluation intelligence". The high power consumption of the prior art measuring devices for the noninvasive determination of peripheral outflow and flow disturbances is due to the fact that the light transmitters have to be triggered with so much current in order that they produce an adequate signal-to-noise interval in the light receivers even if the coupling of the light transmitters to the light receivers via the human skin, whose reflection power is to be measured, is poor. In view of this, the present invention conducts a self-calibration prior to measuring, in which the evaluation and read-out circuit raises the current flowing through the light transmitters until the signal-to-noise ratio in the light receiver attains a specific value. In this manner the light transmitter is always supplied with "just suffiecient" power so that unnecessary energy consumption can be avoided in the portable, hand-held apparatus. The present invention thus permits connecting the optical measuring head, which is placed on the skin, with the actual hand apparatus via an optical fiber, which is critical as a connection line during nonactive control due to its varying losses. The optical fiber thus conveys and directs light from the light transmitter onto the skin of the subject undergoing test and conveys the reflected light to the light receiver.

The present invention permits building a small, portable apparatus than can even be held in one hand and which can be powered at any time by means of batteries or rechargeable accumulators.

In a further embodiment of the present invention, the evaluation and read-out circuit is provided with an active control loop for the current flowing through the light transmitter or transmitters, which is controlled by a microprocessor. In another embodiment, subjective measuring errors are eliminated, which errors are created by incorrectly setting the commencement and termination of the measuring. Additionally, an easy separation of the measurement signal from the surrounding or ambient light is provided to further reduce the energy consumption of the apparatus of the present invention. Read-out of the gained measurement results is provided in an energy-saving manner by using an LCD display unit that can take the form of an eight or multidigit alphanumeric LCD display or a LCD display which permits dot addressing and thereby the representation of graphics etc. The read-out of the measurement results via an electro-acoustic transducer, by way of example, a loudspeaker or earphones, as described in detail in the above cross-referenced and incorporated U.S. Pat. No. 4,836,212 entitled "An Apparatus For the Noninvasive Determination And Acoustic Representation of the Dynamic Behavior of Peripheral Venous Hemodynamic." This type of read-out of the measurement results is not only energy-saving, but also gives the physician a convenient general view of the condition of the blood vessels of the patient undergoing testing in a device having reduced energy consumption requirements.

The evaluation and read-out unit can, in accordance with the present invention, additionally store various activity programs in a memory, which it reads out, by way of illustration, acoustically.

Furthermore, in the case of an acoustical read-out of measurement results, the evaluation and read-out unit can also store a succession of tones, which permits the examining individual to "learn" the interpretation of the acoustical read-out.

The present invention provides a measuring apparatus for the noninvasive determination of peripheral outflow and flow disturbances in the extremities of human beings including at least one light transmitter for directing light onto the skin of a subject undergoing testing and at least one light receiver for receiving reflected light and an evaluation and read-out circuit for ascertaining the temporal course of blood outflow or inflow in the veins by measuring the changes in the reflected light. The evaluation and read-out circuit calibrates itself prior to measuring by raising the current flowing through the light transmitter or transmitters until the signal-to-noise ratio of the receiver has attained a specific value at which time the self-calibration is terminated.

Other objects and further scope of applicability of the present invention will become apparent from the detailed description to follow, taken in conjunction with the accompanying drawings, in which like parts are designated by like reference characters.

DESCRIPTION OF THE PREFERRED EMBODIMENT

Figure 1:
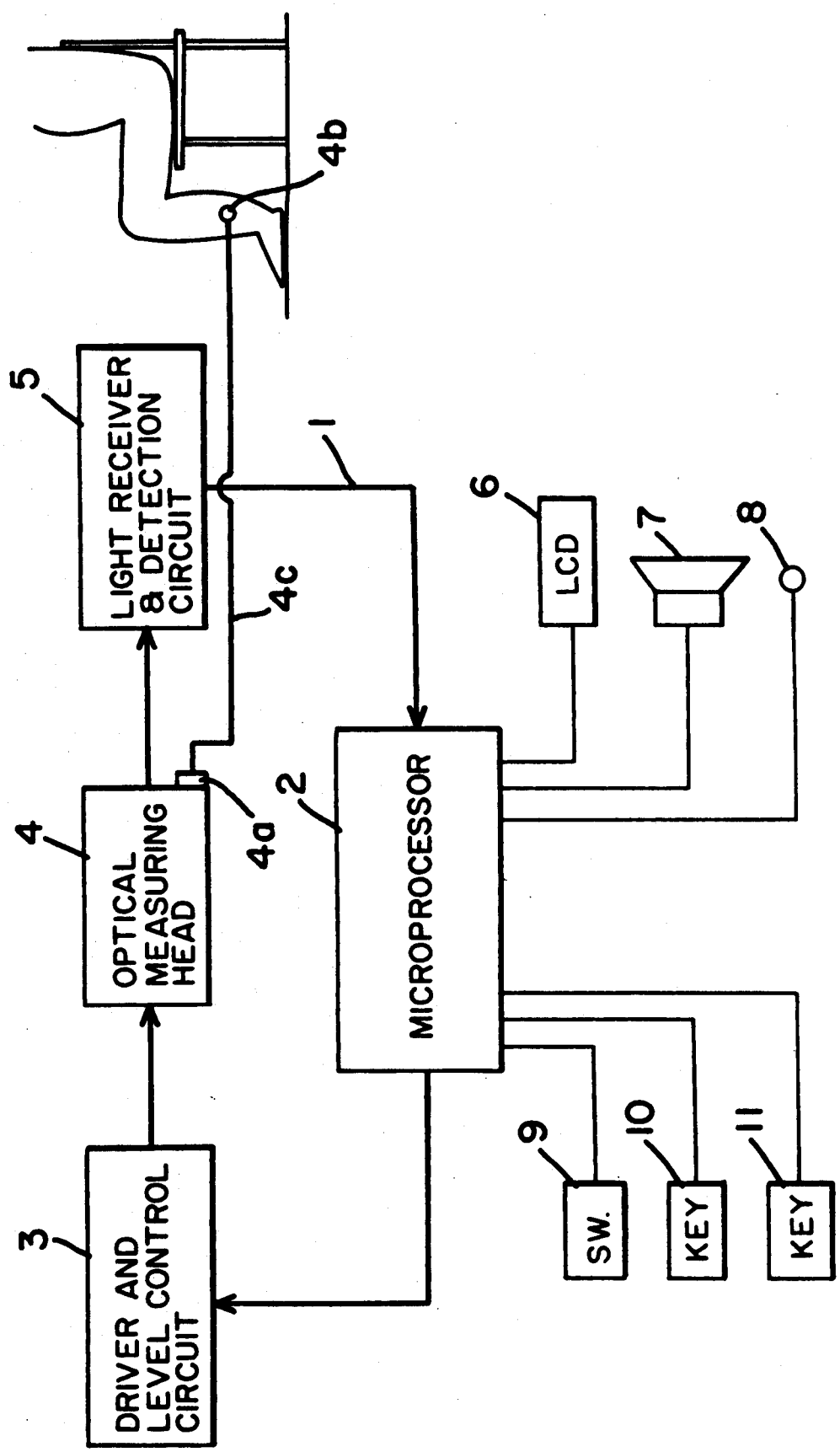
FIG. 1 illustrates a block diagram of the evaluation and read-out unit in accordance with the present invention.

An illustrative embodiment of an evaluation and read-out unit in accordance with the present invention is illustrated in FIG. 1. An active control loop 1 for the current flowing through the light transmitters of an optical measuring head 4 is formed by a microprocessor system 2, a driver and level control unit 3 for the light transmitter or transmitters, the optical measuring head 4 with one or several light transmitters and one or several light receivers, and a reception and detection unit 5 for the signals of the light receiver or receivers of the optical measuring head 4. The measuring head 4 may include a fiber optic sensor 4a for sensing optical signals of a patient at location 4b transmitted via a fiber optic cable 4c.

Drive and level control unit 3 feeds, in a prior art manner, a pulsating current to the light transmitter or transmitters, the "mean value" of which is controlled by the active control loop 1 in such a manner that the microprocessor system controlled signal-to-noise ratio at the output connection of the reception and detection unit 5 "just" reaches a specific value and, accordingly, allows the unit to self-calibrate under various operating conditions. If desired, the current flowing through the light transmitter or transmitters is modulated with a specific frequency and the evaluation and read-out circuit demodulates the output signal from the light receiver or receivers with the same frequency.

Furthermore, a LCD display unit 6, an electro-acoustic transducer 7, by way of illustration, a loudspeaker, a data signal output connection 8, which by way of example can be a standardized transmission reception data connecting point to a printer and/or a calculator, an on/off switch 9, a function select key 10 with which various functions can be switched on or off, as well as a display control key 11, which permits operating display unit 6, have been provided.

Figure 2:
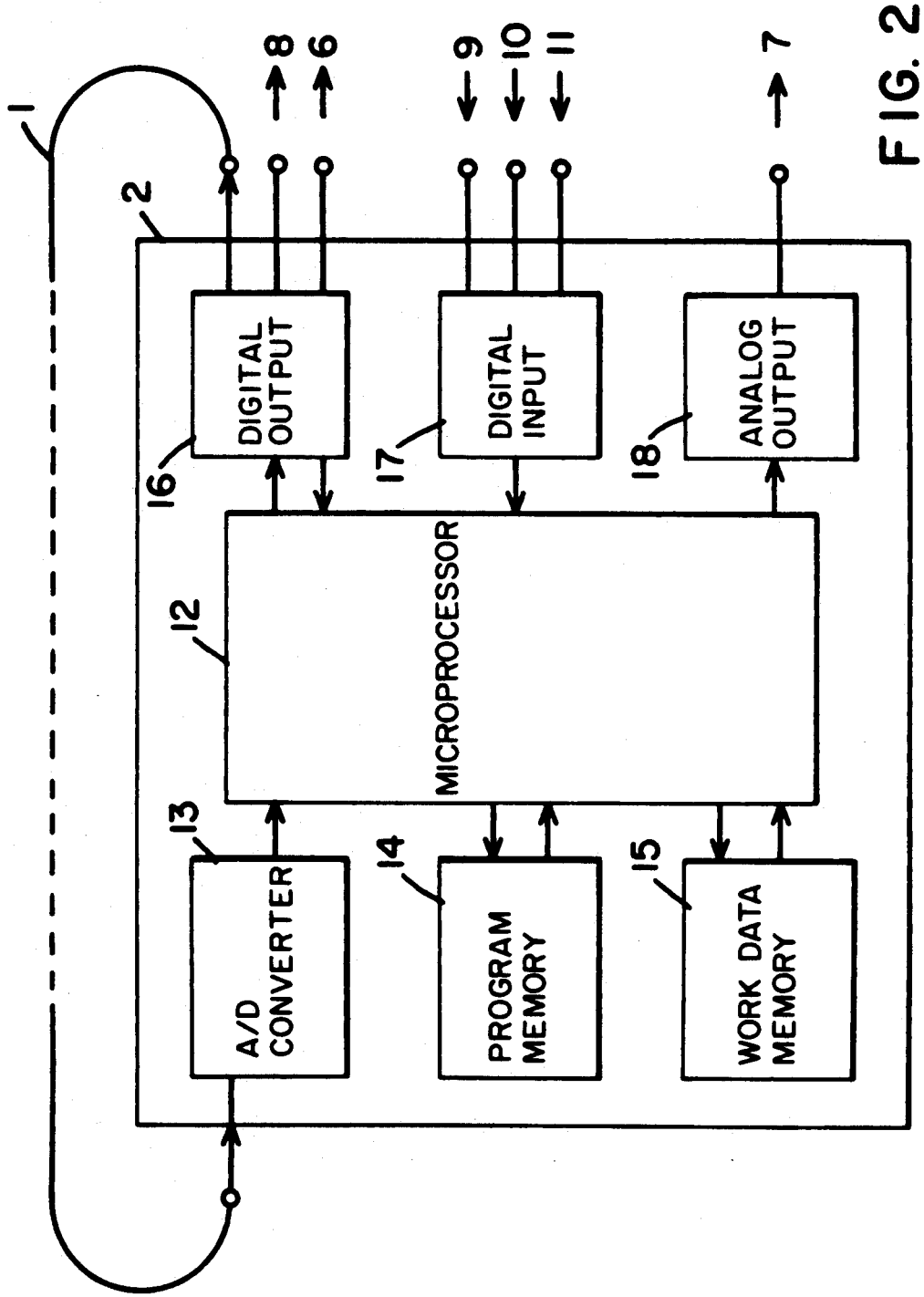
FIG. 2 illustrates a block diagram of an exemplary embodiment of the microprocessor system.

FIG. 2 depicts in detail the construction of an illustrative embodiment of a microprocessor system 2 in accordance with the present invention. Microprocessor system 2 is provided with a microprocessor 12, an analog-to-digital converter 13, which converts the output signals from reception and detection unit 5 for presentation to the microprocessor 12, a program memory 14 for the microprocessor 12, a work and data memory 15, a digital output unit 16, a digital input unit 17, and an analog output unit 18. The connections of elements 16, 17, and 18 to the elements depicted in FIG. 1 are shown in FIG. 2.

Figure 3A:
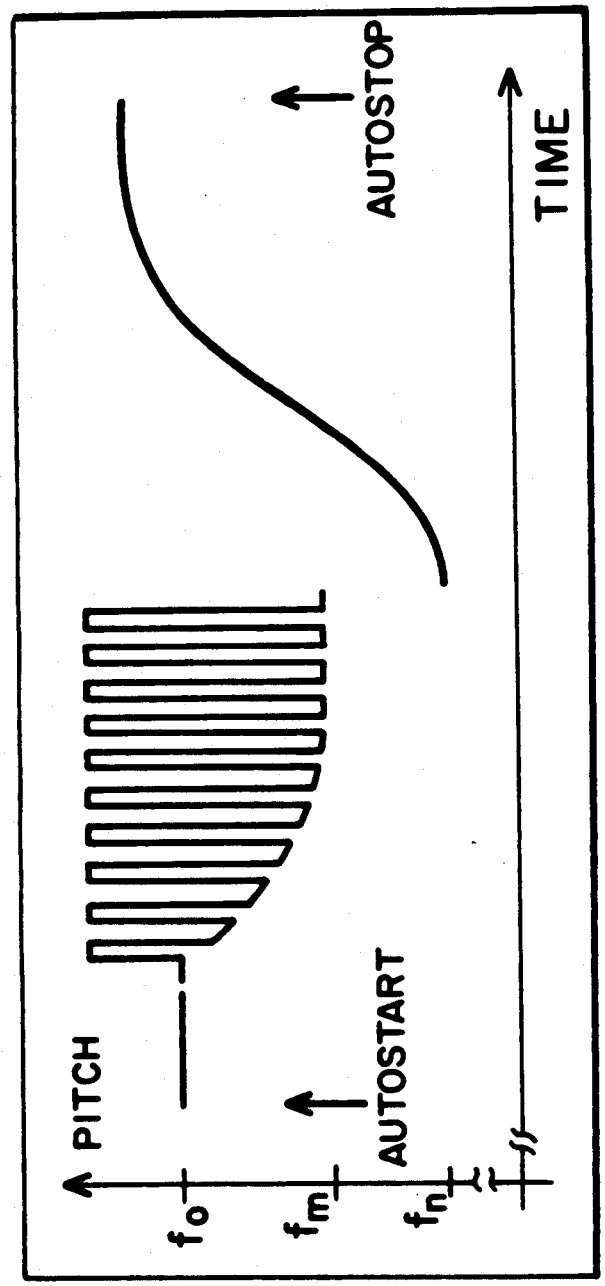
FIGS. 3a, 3b, and 3c shows typical measurement results.

The operating manner of the evaluation and read-out unit schematically illustrated in FIGS. 1 and 2 is made more apparent in the following detailed description in connection with FIG. 3. As described in detail in the above cross-referenced and incorporated U.S. Pat. No. 4,836,212 entitled "An Apparatus For the Noninvasive Determination And Acoustic Representation of the Dynamic Behavior of Peripheral Venous Hemodynamic," the measured reflection signal is converted, by means of the microprocessor 12, analog output unit 18, which can be by way of illustration, a signal amplifier and loud speaker 7, into a succession of tones whose frequency corresponds to the light reflection and thereby the pressure in the blood vessels of the subject undergoing testing. The blood outflow or inflow for which the pressure or the light reflection is a measurement and the resulting pitch of the tone is schematically illustrated in FIG. 3a. The pitch of the tone, thus, represents a measure for the intensity of the measurement signal and not the for frequency shift.

Moreover, microprocessor 12 may control measuring in such a manner so as to inhibit measurement until a quiescent state of blood circulation is reached, and then terminates the measurement when the quiescent state is reached again. To conserve power, the microprocessor includes means to switch off, partially or completely, the current flowing through the light transmitter following a measurement. For record keeping purposes, the microprocessor 12 may additionally include means to assign automatically a consecutive, irreversible number to each measurement. Noninvasive measurement of dynamic behavior of peripheral venus hemodynamics takes place as described in German Patent No. 3,100,610. In particular, the measurement device comprises a sensor which is placed on the skin of the subject in which a luminous diode serves as a light transmitter and a light receiver, e.g., a photo sensitive dial. Reflected light is reflected by different layers of the subject's skin and received by the luminous diode. It is known in the art that the degree of reflection of light is correlated with emptying and filling of the veins, as described in German Patent No. 3,100,610. According to the present invention, the emitted signal from the photosensitive diode is amplified and transposed, e.g., by means of a microcomputer, into a signal the frequency of which is within the sound frequency range of the acoustic spectrum.

Figure 3B:
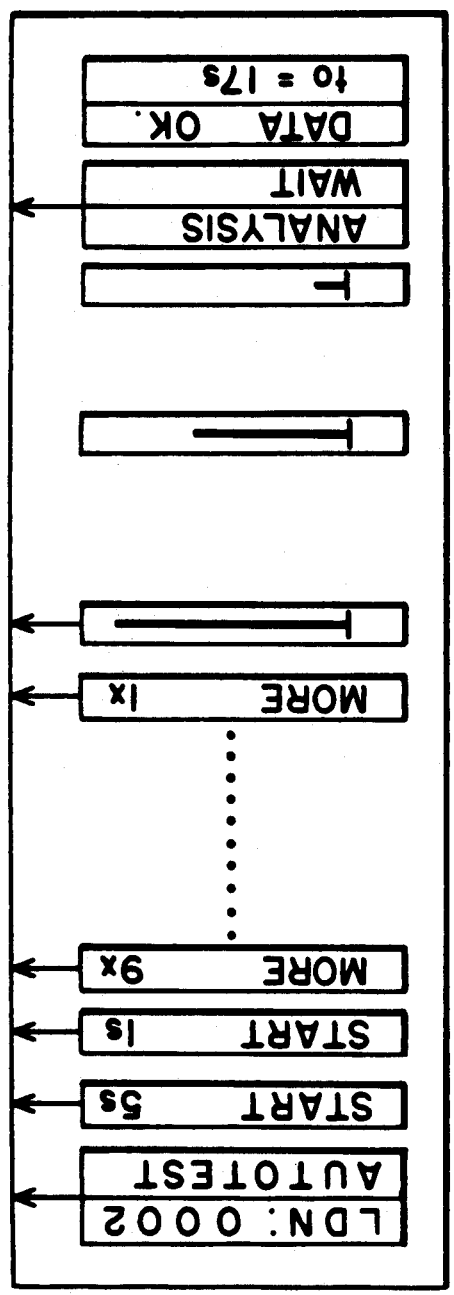

FIG. 3 depicts the reading on the LCD display unit 6 appearing at the respective times. The display unit 6 contains information at the beginning of the measurement indicating a self-calibration is being conducted or how much time will lapse until the measurement is to commence. Subsequently, it shows the number of tones still to be heard during the activity program and, thus, the time remaining for the duration of the activity program. During the inflow phase, the frequency F of the tone as indicated in FIG. 3 represents the level of current skin reflection in an analog manner, by way of illustration, by displaying an analog graph-like bar. Following termination of the inflow phase and a short analysis phase, it indicates, e.g., the duration required for the inflow of the blood vessels until a hemodynamic quiescent state is attained. FIG. 3A represents acoustical read-out data obtained from the measuring apparatus which is derived from a vein pressure curve obtained invasively by means of phlebodynamometry. A first phase occurs at level f and corresponds to constant to blood circulation obtained from a seated patient. A second phase represented by higher frequency signals corresponds to a signal derived while the patient performs movements. A third and final phase following termination of the movement phase corresponds to a rise in blood pressure of the patient.

Figure 3C:
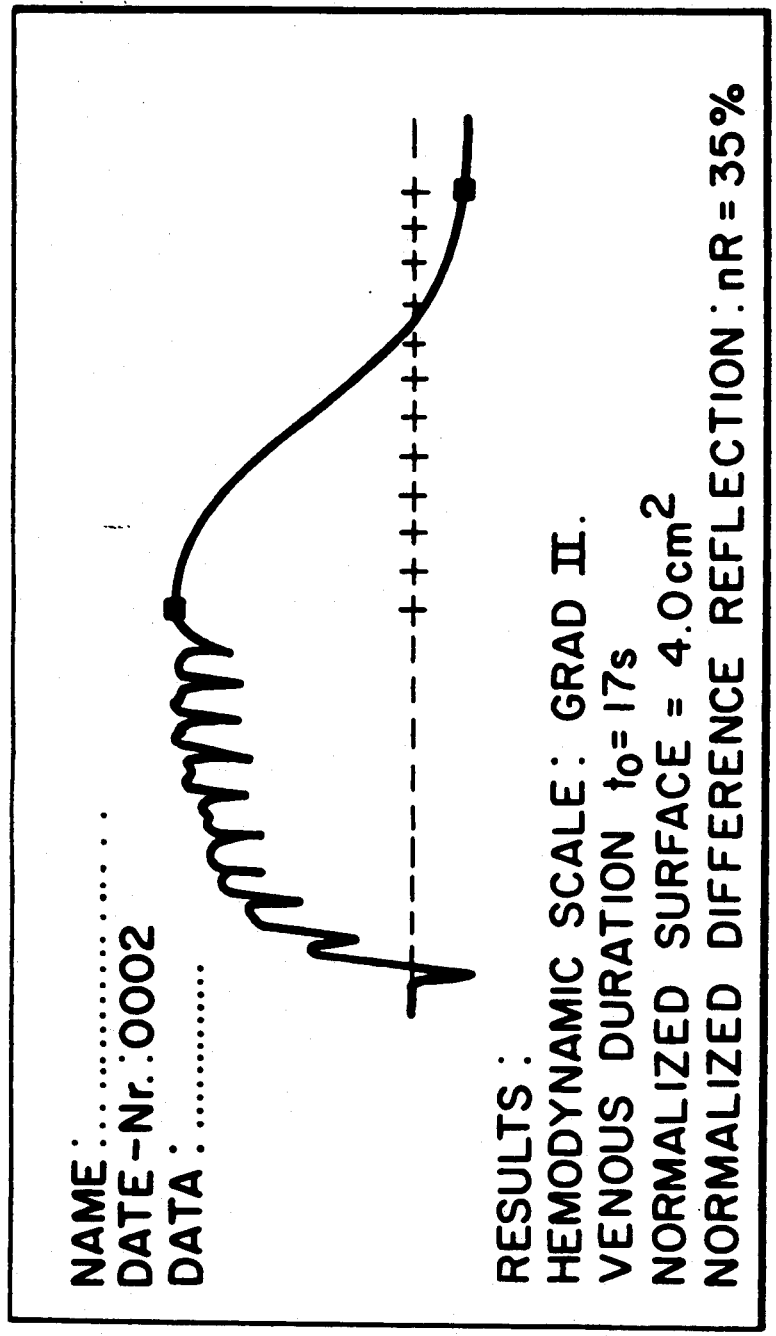

FIG. 3c depicts an example of a read-out received on an external printer connected to the measuring apparatus of the present invention via the output connection 8. The measurement values are read-out and, if desired, the parameters calculated by the microprocessor 12 can also be read-out.

The present invention has been described hereinbefore in connection with a preferred embodiment of the invention by way of illustration only without any intention to limit the scope of the invention. The most varied modifications are, of course, possible within the scope of the inventive idea. By way of example, the self-calibration conducted prior to commencement of the measuring can include not only the setting of a specific signal-to-noise ratio and, in the case of an acoustical read-out, the setting of a specific pitch of the tone, but also a "zero balance" of the entire analog electronic components conducted by the digital section. Furthermore, the operational processes program packages stored in the program memory of microprocessor system 2 can contain not only the mode of measuring and a read-out mode, but also a "learning program", which trains the operating staff to acoustically discern specific acoustically converted hemodynamic processes as often as one likes. The selection of individual program packages can be made via the function select key 10.

Furthermore, the read-out and/or the acoustical representation can be switched off by means of the display control key 11 so that, if necessary, energy consumption can be further reduced.

In any case, the inventive concept makes it possible to build a compact and an easy to handle apparatus that can be held in one hand at any time and can be used at different locations.

Thus it will be appreciated from the above that as a result of the present invention, a highly effective microprocessor controlled apparatus for the noninvasive determination of peripheral outflow and flow disturbances is provided by which the principal objective, among others, is completely fulfilled. It will be equally apparent and is contemplated that modification and/or changes may be made in the illustrated embodiment without departure from the invention. Accordingly, it is expressly intended that the foregoing description and accompanying drawings are illustrative of preferred embodiments only, not limiting, and that the true spirit and scope of the present invention will be determined by reference to the appended claims and their legal equivalent.

What is claimed is:

1. A measurement apparatus for the noninvasive determination of peripheral blood outflow and flow disturbances in veins of human beings, said apparatus including at least one light transmitter and one light receiver for directing and receiving reflected light from an extremity of said being, an evaluation and read-out circuit to ascertain blood outflow and inflow in the veins by means of measuring the change in light reflection, said evaluation and read-out circuit including means to raise, prior to said measuring, the current flowing through the light transmitter until the signal-to-noise ratio of the receiver has attained a specific value.

2. An apparatus according to claim 1, whereby said evaluation and read-out circuit is provided with a microprocessor controlled active control loop for said current flowing through the light transmitter.

3. An apparatus according to claim 1, whereby said evaluation and read-out circuit includes means for inhibiting commencement of measuring until a quiescent state of the blood circulation in the skin has been registered.

4. An apparatus according to claim 1, whereby said current flowing through the light transmitter is modulated with a specific frequency and said evaluation and read-out circuit demodulates the output signal from the light receiver or receivers with the same frequency.

5. An apparatus according to one of the claim 1, whereby said evaluation and read-out circuit is provided with a LCD display unit.

6. An apparatus according to claim 1, whereby said display and evaluation circuit is provided with an electro-acoustic transducer for reading out the measuring results.

7. An apparatus according to claim 1, whereby said display and evaluation circuit terminates the measuring when a quiescent state of the blood circulation in the skin is registered again.

8. An apparatus according to claim 1, whereby said evaluation and read-out circuit switches off, completely or partially, the current flowing through the light transmitter following a measurement.

9. An apparatus according to claim 1, whereby said evaluation and read-out unit stores several activity programs, which it emits acoustically.

10. An apparatus according to claim 1, whereby said evaluation and read-out unit stores a learning-succession of tones.

11. An apparatus according to claim 1, whereby the optical measuring head is embodied as a fiber optical sensor.

12. An apparatus according to claim 1, whereby said evaluation and read-out circuit automatically assigns each measurement a consecutive, irreversible number.

* * * * *